United States Patent [19]

Welber et al.

[11] Patent Number: 4,605,280
[45] Date of Patent: Aug. 12, 1986

[54] UNIVERSAL LIGHT CABLE ADAPTER FOR LIGHT SOURCE

[75] Inventors: Stanley Welber, Palatine; Nick Lakatos, Des Plaines, both of Ill.

[73] Assignee: Eder Instrument Company, Inc., Chicago, Ill.

[21] Appl. No.: 736,517

[22] Filed: May 20, 1985

Related U.S. Application Data

[63] Continuation of Ser. No. 400,343, Jul. 21, 1982, abandoned.

[51] Int. Cl.$^4$ ............................. G02B 6/36; G02B 7/26
[52] U.S. Cl. ................................. 350/96.20; 350/96.22; 350/96.23; 350/96.24; 350/96.26; 128/395; 128/396
[58] Field of Search ............... 350/96.10, 96.18, 96.20, 350/96.21, 96.22, 96.23, 96.24, 96.25, 96.26, 96.27; 362/32; 279/66; 128/395, 396, 397, 398, 4, 5, 6, 7, 8, 9

[56] References Cited

U.S. PATENT DOCUMENTS

| | | | |
|---|---|---|---|
| 3,914,013 | 10/1975 | Rosenberg | 350/96.18 |
| 3,999,841 | 12/1976 | Dakss et al. | 350/96.20 |
| 4,025,776 | 5/1977 | Cawood et al. | 350/96.24 |
| 4,189,233 | 2/1980 | Hurt et al. | 350/96.18 |
| 4,208,095 | 6/1980 | Malsot | 350/96.22 |
| 4,213,671 | 7/1980 | Lambert | 350/96.21 |
| 4,232,934 | 11/1980 | Feinbloom | 350/96.20 |
| 4,276,113 | 6/1981 | Carlsen et al. | 350/96.21 |
| 4,302,071 | 11/1981 | Winzer | 350/96.20 |
| 4,397,523 | 8/1983 | Feinbloom et al. | 350/96.20 |

FOREIGN PATENT DOCUMENTS 2071867 9/1981 United Kingdom ............. 350/96.20

OTHER PUBLICATIONS

Wolf Co., "Fiber Light Projector" advertisement (no date) p. 1.

Primary Examiner—William L. Sikes
Assistant Examiner—Brian M. Healy
Attorney, Agent, or Firm—Andrus, Sceales, Starke & Sawall

[57] ABSTRACT

Endoscopes employ an optical fiber cable connected to a light source to illuminate the viewing field. The adapter of the present invention facilitates connection of the optical fiber cable to the light source by accommodating a wide variety of differing cable connector sizes and types. The adapter has a channel-like frame mounted on the light source in front of the light. A cable holder with a downwardly opening notch is mounted on one flange of the frame. A spring biased cable support with an upwardly opening notch is mounted adjacent the cable holder so that the notches form an opening in which the connector may be engaged and retained in the adapter.

7 Claims, 6 Drawing Figures

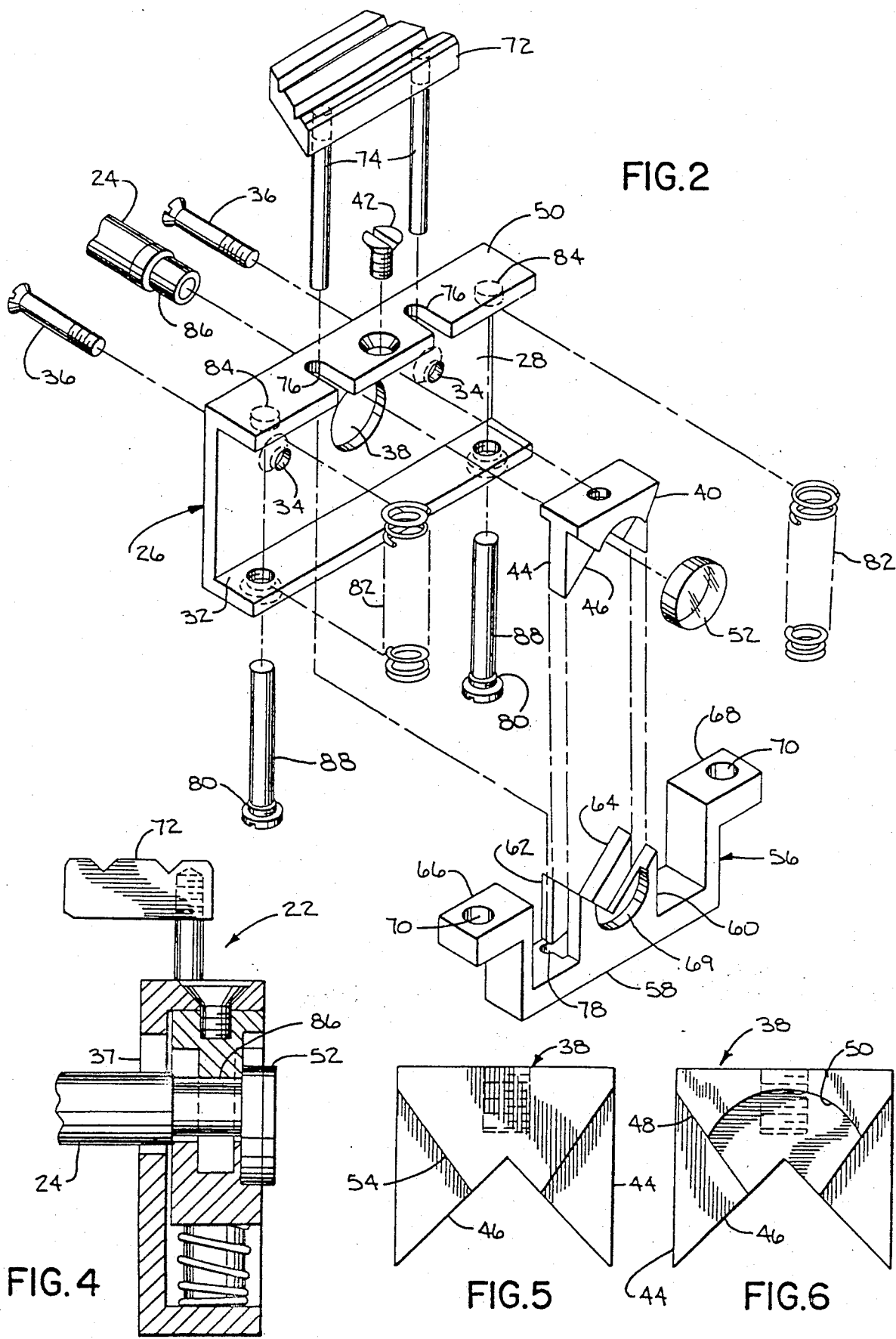

UNIVERSAL LIGHT CABLE ADAPTER FOR LIGHT SOURCE

This application is a continuation of application Ser. No. 400,343, filed July 21, 1982, now abandoned.

BACKGROUND OF THE INVENTION

Optical instruments such as endoscopes, laparoscopes, arthroscopes, bore scopes, and the like contain a bundle of optical fibers that conducts light down the scope and provides illumination to the viewing field. The fiber bundle in the scope is coupled at the eyepiece end of the scope to a flexible optical fiber cable that is connected to a light source containing the illuminating lamp.

A number of flexible optical fiber cables are in use having varying sizes according to the type and make of the instrument with which they are used. The cables have differing types of connectors to the light source, also depending on the type, size, and make of cable, instrument, and/or light source. This causes problems in connecting the optical fiber cable to the light source because of incompatibility of the connector on the cable to that on the light source. A different light souce may have to be provided for each different optical fiber cable or the connectors on each of the cables must be changed to a single, common fitting that will connect with the light source. Either of these alternatives is expensive and awkward.

Various techniques have been devised to accommodate the different types of cable connectors. In one such arrangement, a disc is provided on the front of the light source having a variety of arcuately spaced connectors of different types. The connector needed for the type of optical fiber cable in use is indexed to a position in front of the lamp in the light source to provide a connection for the cable and illumination to the scope. However, even with the variety of connectors on the disc, a suitable connector may not be available for all the cables presently in use or coming into use, so that again, different light sources will be required, or the cable connectors must be changed.

SUMMARY OF THE INVENTION

It is, therefore, the object of the present invention to provide an improved adapter that facilitates connection of the optical fiber cable to the light source by accommodating a wide variety of differing cable sizes and connectors formats without modification. The adapter thus approaches universiality in use.

Briefly, the present invention provides an adapter having a frame mountable on the light source in front of the light. The frame may be channel-like in form. A cable holder is mounted on the frame and has a first surface element, for example, in the form of a downwardly opening notch for receiving the optical fiber cable connector. A cable support is relatively movable with respect to the cable holder and has a second surface element in the form of an upwardly opening notch forming an opening with the notch of the cable holder for engaging a connector inserted in the adapter. Spring means bias the cable holder and cable support together for retaining the connector in the adapter. Preferably the cable support has a pair of members embracing the cable holder on either side. A glass disc is interposed between the ends of the optical fibers in the cable and the light of the light source. An operating bar is used to move the cable support away from the cable holder against the bias of the springs to permit insertion of the cable connector.

BRIEF DESCRIPTION OF THE DRAWING

The invention will be further explained by the aid of the accompanying drawings in which:

FIG. 2 is an exploded perspective view of the adapter of the present invention taken from the rear;

FIG. 4 is a cross sectional view taken along the line 4—4 of FIG. 3; and

FIGS. 5 and 6 are front and rear views, respectively, of the cable holder element of the adapter.

DETAILED DESCRIPTION OF THE INVENTION

Figure 1:
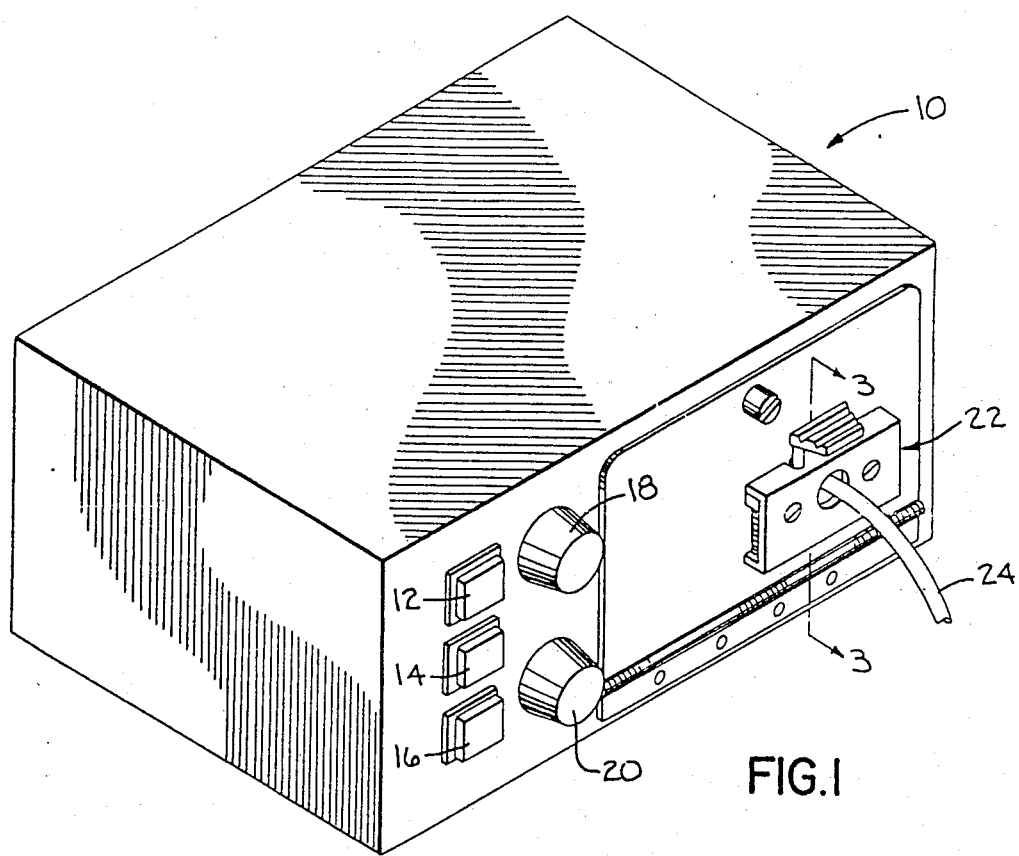
FIG. 1 is a perspective view of an optical fiber light source utilizing the adapter of the present invention.

In FIG. 1, the numeral 10 indicates a light source for an endoscope or other optical instrument. Light source 10 includes switches 12, 14, and 16 for turning the light source on and off and for selecting lamps of various wattage. Control knobs 18 and 20 control the intensity of the illumination established by the lamps. Universal adapter 22 receives fiber optic cable 24 for supplying the illumination from the lamps in light source 10 to the endoscope or other instrument, not shown.

Figure 3:
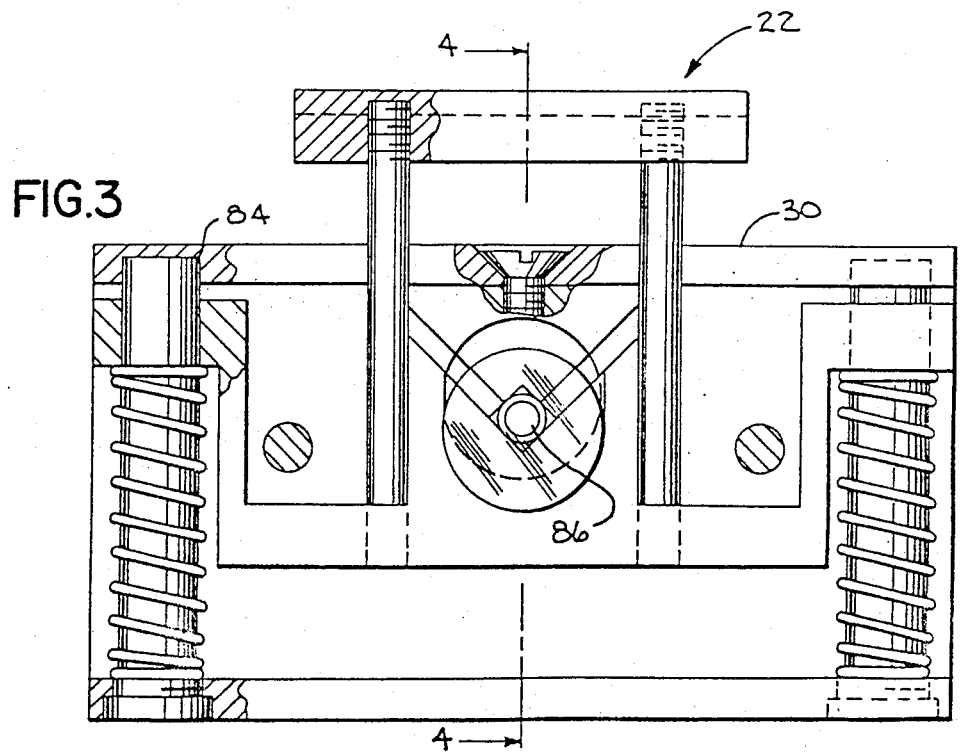
FIG. 3 is a rear view, partially cut away, of the adapter of the present invention.

As shown in FIGS. 2, 3, and 4, universal adapter 22 includes a channel-like frame 26 having web 28, upper flange 30, and lower flange 32. Web 28 contains holes 34 for receiving fasteners 36 that secure universal adapter 22 to light source 10. Web 28 also contains hole 38 through which cable 24 is inserted, as hereinafter described.

Cable holder 40 is fastened to the underside of upper flange 30 by fastener 42. The cable holder extends downwardly from the upper flange. Cable holder 38 has a central plate 44, spaced from web 38 dontaining downwardly opening V-shaped notch 46 subtending an angle of 90°. As shown in FIG. 6, the side of plate 44 away from web 28 contains a thickened portion 48 that contains an arcuate cut-out 50 for receiving light conduting glass disc 52. The side of plate 44 toward web 28 contains a thickened portion 54 that tapers downwardly toward an upwardly pointing notch that follows the contours of notch 44. See FIG. 5.

Cable support 56 has a medial portion 58 with a pair of spaced members 60 and 62 that embrace central plate 44 on both of its sides. Members 60 and 62 contain upwardly opening 90° notch 64. Flange 60 contains a generally semi-circular cut out 69 in which galss disc 52 rests. Glass disc 52 is fastened to cable support 56 by adhesive or other means. Medial portion 58 may be cut out between members 60 and 62. Medial portion 58 terminates in a pair of arms 66 and 68 of inverted L configuration. Arms 66 and 68 contain holes 70.

Operating bar 72 has spaced, depending rods 74 extending through slots 76 in upper flange 30. Rods 74 are press fitted into holes 78 in medial portion 58 of cable support 56.

Rods 88 extend through lower flange 32 and are secured by threads 80. Springs 82 surround rods 88. Rods 88 pass through holes 70 in arms 66 and 68 so that the arms are biased upwardly by the springs. Rods 88 terminate in recesses 84 in upper flange 30.

If no optical fiber cable is inserted in adapter 22, cable support 56 is biased upwardly until arms 66 and 68 abut the underside of upper flange 30. Members 60 and 62 are contiguous with plates 44 and 56 of cable holder 40. Glass disc 52 rests in cut out 50.

To couple connector 86 of optical fiber cable 24 to light source 10, operating bar 72 of adapter 22 is depressed to lower cable support 56 against the bias of springs 82. Connector 86 of cable 24 is inserted through hole 38 in flange 28 into the opening formed by notches 46 and 64. Bar 72 is released to allow cable support 56 to move upwardly so that connector 86 is clamped between cable holder 40 and the cable support, as shown in FIGS. 3 and 4. Glass disc 52 rides with cable support 56 to prevent connector 86 from being inserted into light source 10 with the attendant possiblity of damaging the lamps. Light from the lamp in light source 10 passes through glass disc 52 and into the fibers of the cable.

The opening formed by notches 46 and 64 in cable holder 40 and cable support 56 can easily accommodate cable connectors of different sizes and shapes, thus facilitating connection of a variety of cables 24 to light source 10 through the use of adapter 22.

Various modes of carrying out the invention are contemplated as being within the scope of the following claims particularly pointing out and distinctly claiming the subject matter which is regarded as the invention.

We claim:

1. An adapter for coupling optical fiber cables having connectors of differing types and sizes to a light source, said adapter comprising:
    a frame mountable on said light source in front of the light of the source,
    a cable holder mounted on said frame and having a first stationary surface element capable of receiving an optical fiber cable connector;
    a cable support operatively associated with said cable holder and including a second surface element disposed in opposition to said first surface element and capable of receiving the optical fiber cable connector, said cable support relatively movable with respect to said cable holder between a first unclamped position and a second clamped position so that said second surface element coacts with said first surface element to clamp therebetween connectors of differing types and sizes inserted in said adapter;
    spring means biasing said second surface element toward said second clamped position for retaining the optical fiber cable connector in said adapter;
    actuator means for moving said cable support against the force of said spring means; and
    stop means for preventing a connector from engaging and possibly damaging the light source when inserted between said cable holder and cable support, said stop means includes a light transmitting disc member mounted on said cable support for movement therewith and positionable in axial alignment with said connector between said connector and said light source when said connector is retained in said adapter.

2. The adapter of claim 1 wherein said first surface element is in the form of a first notch opening in a given direction, wherein said second surface element is in the form of a second notch opening in the opposite direction, and wherein the connector is engaged and retained in an opening formed by the mutual coaction of said notches.

3. The adapter of claim 2 wherein said cable holder and cable support are positioned adjacent to each other in a direction normal to the direction of relative movement of the cable support to form an opening lying normal to said direction of relative movement.

4. The adapter of claim 3 wherein said cable holder has a central plate containing said first notch and wherein said cable support has a pair of members containing second notches and embracing said plate on either side thereof.

5. The adapter of claim 2 wherein each of the notches is formed to subtend a 90° angle.

6. The adapter of claim 1 wherein said frame is channel-like in form and contains said cable holder and cable support.

7. An adapter for coupling optical fiber cables having connectors of differing types and sizes to a light source, said adapter comprising:
    a frame mountable on said light source in front of the light of the source,
    a cable holder mounted on said frame and having a first stationary surface element capable of receiving an optical fiber cable connector;
    a cable support operatively associated with said cable holder and including a second surface element disposed in opposition to said first surface element and capable of receiving the optical fiber cable connector, said cable support relatively movable with respect to said cable holder between a first unclamped position and a second clamped position so that said second surface element coacts with said first surface element to clamp therebetween connectors of differing types and sizes inserted in said adapter;
    spring means biasing said second surface element toward said second clamped position for retaining the optical fiber cable connector in said adapter;
    actuator means for moving said cable support against the force of said spring means, said actuator means includes a bar member movable towards said connector to move said cable support away from said cable holder to said first unclamped position; and
    stop means for preventing a connector from engaging and possibly damaging the light source when inserted between said cable holder and cable support, said stop means includes a light transmitting disc member mounted on said cable support for movement therewith and positionable in axial alignment with said connector between said connector and said light source when said connector is retained in said adapter.

* * * * *